United States Patent [19]

Slonicki

[11] 4,190,472

[45] Feb. 26, 1980

[54] AUTOMATED SYSTEM FOR THE APPLICATION OF COVERGLASSES ON HISTOLOGICAL AND CYTOLOGICAL SLIDES

[76] Inventor: Alex Slonicki, 86 Bacon St., Winchester, Mass. 01890

[21] Appl. No.: 837,642

[22] Filed: Sep. 28, 1977

[51] Int. Cl.² ........................ A65C 9/08; A01N 1/00
[52] U.S. Cl. ...................................... 156/57; 156/99; 156/357; 156/358; 156/542; 156/566; 156/569; 156/578; 211/41; 221/73; 221/82; 221/90; 271/162
[58] Field of Search ................. 156/57, 542, 540, 541, 156/344, 584, 99, 108, 356, 357, 358, 578, 360–364, 366, 566, 569, 570; 221/73, 186, 91, 90, 84, 85, 82, 76, 79; 427/4, 2; 271/162; 206/456; 424/3; 211/41, 60 A; 269/55, 56; 198/540; 118/500

[56] References Cited

U.S. PATENT DOCUMENTS

| 2,783,180 | 2/1957 | Whitehead | 156/57 |
|---|---|---|---|
| 3,138,508 | 6/1964 | Fairest | 156/285 |
| 3,493,447 | 2/1970 | Rock | 156/57 |
| 3,682,083 | 8/1972 | Puente | 118/500 |
| 3,939,019 | 2/1976 | Pickett | 156/57 |
| 4,033,809 | 7/1977 | Tipton | 156/57 |
| 4,034,700 | 7/1977 | Bassett et al. | 118/7 |
| 4,049,342 | 9/1977 | Hearon | 271/DIG. 9 |
| 4,103,041 | 7/1978 | Macho et al. | 427/2 |

Primary Examiner—Michael W. Ball
Attorney, Agent, or Firm—Haseltine, Lake & Waters

[57] ABSTRACT

A system for processing and finishing stained glass slides includes a staining rack for receiving stained slides and including a device for discharging the stained slides therefrom, a conveyor for receiving the discharged stained slides from the staining rack, and for transporting the stained slides in a direction away from the staining rack; and a slide finishing station cooperating with the conveyor. The slide finishing station includes a device for depositing glue onto the stained slide; the stained slide carries the glue, and a device is provided for applying a cover glass to the glue-carrying slide.

9 Claims, 7 Drawing Figures

AUTOMATED SYSTEM FOR THE APPLICATION OF COVERGLASSES ON HISTOLOGICAL AND CYTOLOGICAL SLIDES

BACKGROUND OF THE INVENTION

1. Field of the Invention

This invention relates to a system for finishing stained glass slides. More particularly this system comprises a staining rack for receiving stained slides from which such slides are discharged; a conveyor means for transporting such slides to a finishing station; and a slide finishing station for applying a cover glass to said slide.

2. Description of the Prior Art

There is known from U.S. Pat. No. 2,783,180 a tissue-holder receptacle for use in treating tissue with a processing liquid and the preparation of tissue for microscopic examination. It includes a container which has an internal surface, a part of it being formed of porous fibrous material for mounting the tissue thereon in position for access thereto of processing liquid within the container. The porous fibrous material has a plurality of openings for access of the liquid to the tissue.

From U.S. Pat. No. 2,837,055 there is known a tissue-holder receptacle for use in treating tissue with a processing liquid in the preparation of the tissue for microscopic examination, which includes a container which has an internal surface a part of which is formed of porous fibrous material for mounting the tissue thereon, and a perforated surface part provided for access of the processing liquid to the tissue. A removable liner has perforations of smaller size than the perforations on the container surface part and the liner may be positioned adjacent to the perforated surface part for preventing small tissue specimens from passing out of the container through the perforations in the surface part.

From U.S. Pat. No. 3,138,508 there is known a method for applying to an article a label and a sheet of material to be enclosed between the label and the article which includes applying gum marginally to one face of a label to leave an ungummed central area that extends longitudinally to at least one ungummed margin. The label has a hole through the area, holds the ungummed face of the label by suction, presents to the ungummed central area a sheet of material less in width than that area, and holds it to the label by suction applied through the hole in the label, and applies the combined assembly of marginally-gummed label and suction-sheet of material to an article.

From U.S. Pat. No. 3,582,437 it is known that the surface speed of rapidly moving, spaced-apart blanks can be reduced without reducing the rate of succession by decreasing the blank spacing, even to the extent of partial overlapping, by leaving the tunnel window area exposed. The rotating patch gum applicators operate on the blanks at a conventional surface speed while other operations on the blanks may be performed in the envelope machine at higher surface speeds. From U.S. Pat. No. 3,493,447 there is known a method and an apparatus for the preparation of specimens of cellular or particular substances suspended in the liquid for microscopic examination which consists in applying a series of traces of the respective specimens onto a transparent film by drawing them on the film, and fixing the series of traces on the film.

From U.S. Pat. No. 3,682,083 there is known an open frame processing rack for photographic glass plates which has a pair of gripping rollers with annular grooves for engaging opposite edges of the plates. The rollers are resiliently biased against the edges of the plates and the depth of insertion of the plates between the rollers is limited.

Finally, from U.S. Pat. No. 3,939,019 there is known a covering apparatus and method directed to applying transparent adhesive tape over strained serial tissue sections which have been mounted on motion picture type film. The tape serves as a protective cover for the sections in lieu of glass lights, plastic and glass cover slips, plastic sprays and the like.

SUMMARY OF THE INVENTION

A system for processing and finishing stained glass slides includes a staining rack for receiving stained slides and a device for discharging the stained slides therefrom. A conveyor belt is used for receiving the discharged stained slides from the staining rack and for transporting the stained slides in a direction away from the staining rack. A slide finishing station cooperates with the conveyor and the slide finishing station includes a device for depositing glue onto the stained slide. The stained slide carries the glue, and a device is provided for applying a cover glass to the glue carrying slide.

The staining rack includes a longitudinal frame which has a floor. The floor has first and second longitudinal edges, and first and second longitudinal bars are attached to the floor in the vicinity of the first and second longitudinal edges, respectively. Each of the bars has an inner side. The staining rack includes an even number of longitudinal slide holder elements which have first and second end portions, respectively; the first end portions of one half of the slide holder elements are pivotally attached to the inner side of the first bar, and the first end portions of the remaining half of the slide holder elements are pivotally attached to the inner side of the second bar. Third and fourth longitudinal bars are pivotally attached to the second end portions of the slide holder elements, and at least one link joins the third and fourth bars. The slide holder elements are then movable in unison from a first position inclined at a first angle from the vertical to a second position inclined at a second angle from the vertical.

Each of the slide holder elements is formed with a rack-inwardly facing longitudinal groove, and the floor is formed with a plurality of slits. Each of the slits extend from approximately the pivotal attachment of one of the slide holder elements to the first bar, to the pivotal attachment of another of the slide holder elements to the second bar. The latter two slide holder elements are disposed opposite one another and a slide may be inserted therebetween.

Each of the slide holder elements is formed with at least a first slanted edge and the first slanted edge acts as a limit stop and abuts the floor in the first position of the slide holder element.

Each of the slide holder elements is formed also with a second slanted edge, and the second slanted edge is substantially symmetrical with the first slanted edge above the longitudinal groove.

A second link joins the third and fourth bars and is disposed opposite the first link.

The system additionally includes a housing which has first and second longitudinal portions and a housing end portion joins the longitudinal portions. The first and second longitudinal bars are attached to the first and second longitudinal portions, respectively. The end portion acts as a limit stop in the second position of the slide holders.

The conveying means includes a rack formed with an opening, and the staining rack may be moved across the opening. The slide-holder elements are in one of the first and second positions, and the rack opening is sufficiently wide for a slide inserted into the staining rack slide holder elements to drop therethrough.

A first propelling means is disposed below the rack and a second propelling means has an inclined position and may be placed in the vicinity of the rack and of the first propelling means. The dropped slide then lands on the second propelling means, and is pushed by the latter onto the first propelling means. Successively dropped slides occupy separable positions on the second propelling means, and the latter may be moved at a predetermined velocity.

The first propelling means includes first and second rollers, and a continuous first belt links the rollers. A plurality of ridges are disposed on the belt for a slide to be positioned between adjacent ridges. The second propelling means includes third and fourth rollers, and a continuous second belt links the third and fourth rollers. Other alternative propelling means for transporting slides can also be employed and are within the purview of this invention.

The means for depositing glue onto the stained slide preferably includes peristaltic dispenser means which may be activated when the slide has reached a predetermined position. The means for applying a cover glass to the stained slide includes a tape which has a glass-adhesive property and may be moved at a predetermined velocity. The cover glass may be attached to the tape, and the tape with the attached cover glass may be positioned and passed over the first propelling means so that the cover glass can be aligned and may make contact with one of the dropped slides. Roller means can pass over the cover-glass holding tape, and the latter can be positioned over the one of the dropped slides for exerting pressure on the tape for the cover glass to be transferred from the tape to the stained slide. The glue has an adhesive property which exceeds the adhesive property of the tape. A set of heatable pressure rollers is disposed in the vicinity of the roller means, and the stained slide which has a cover glass attached thereto can be passed over a support and below the pressure rollers for the slide and the cover glass to be laminated together.

BRIEF DESCRIPTION OF THE DRAWING

My invention will be better understood with respect to the accompanying drawing in which.

DESCRIPTION OF THE PREFERRED EMBODIMENTS

Figure 1:
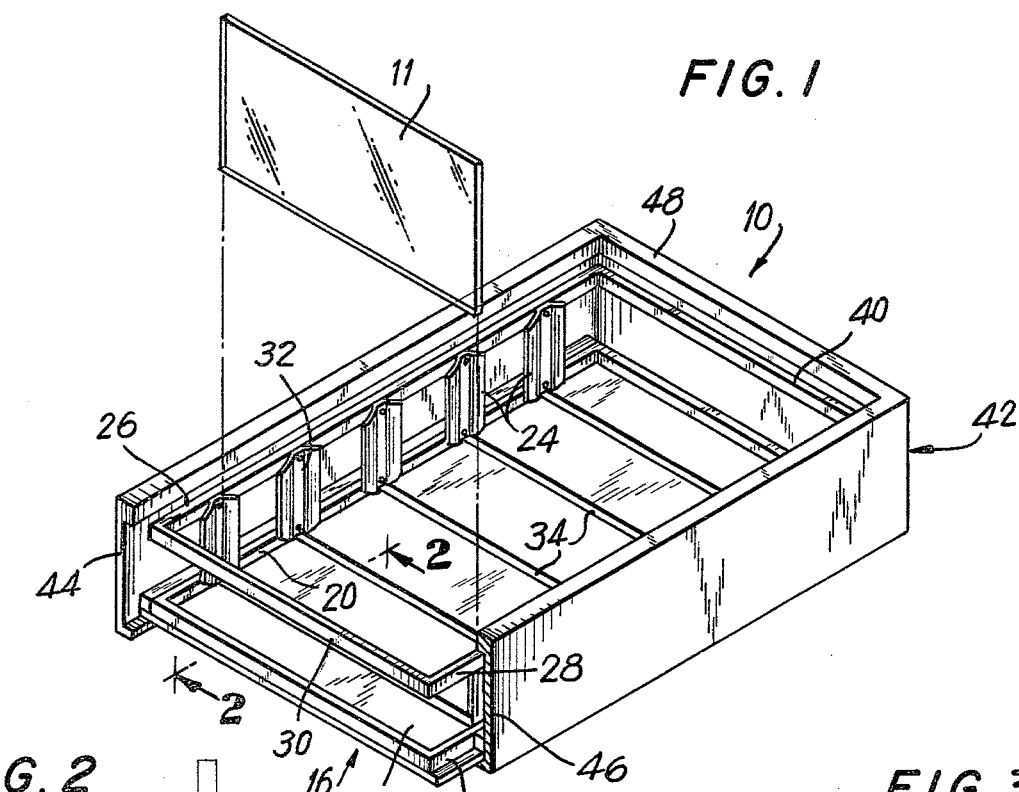
FIG. 1 shows a perspective view of the staining rack.
Figure 5:
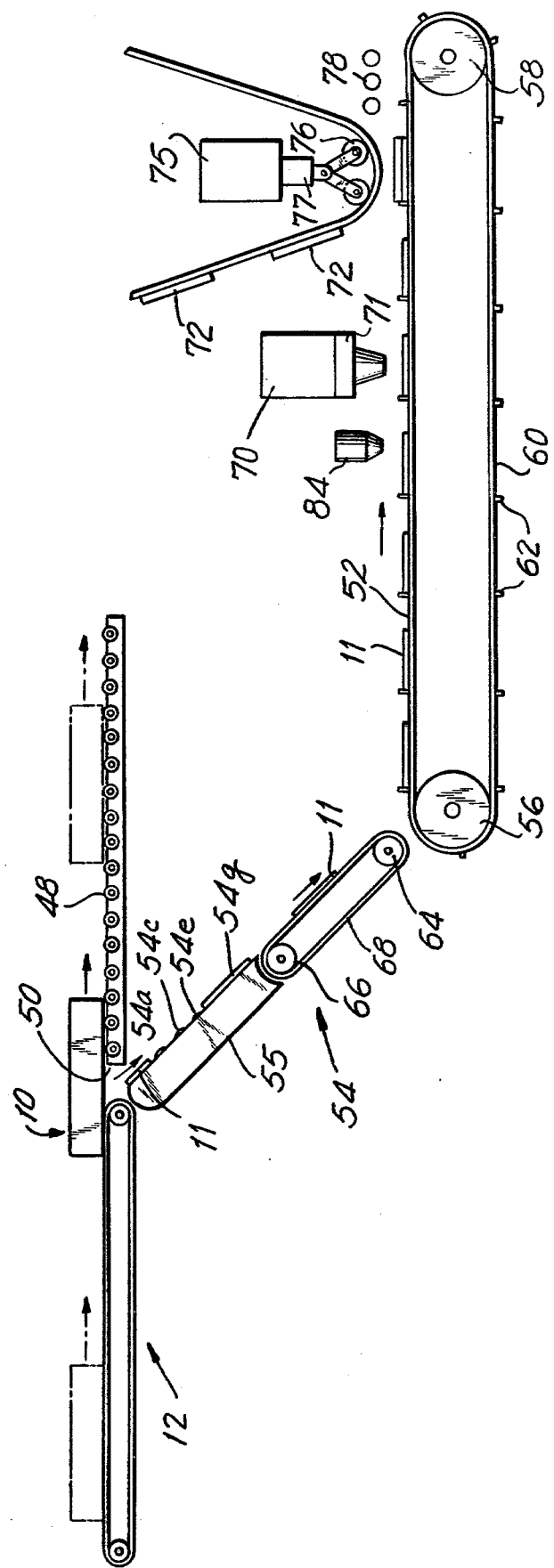
FIG. 5 shows the conveyor for the staining rack, the inclined endless belt for removing the slide and the slide finishing station in diagrammatic form.
Figure 6:
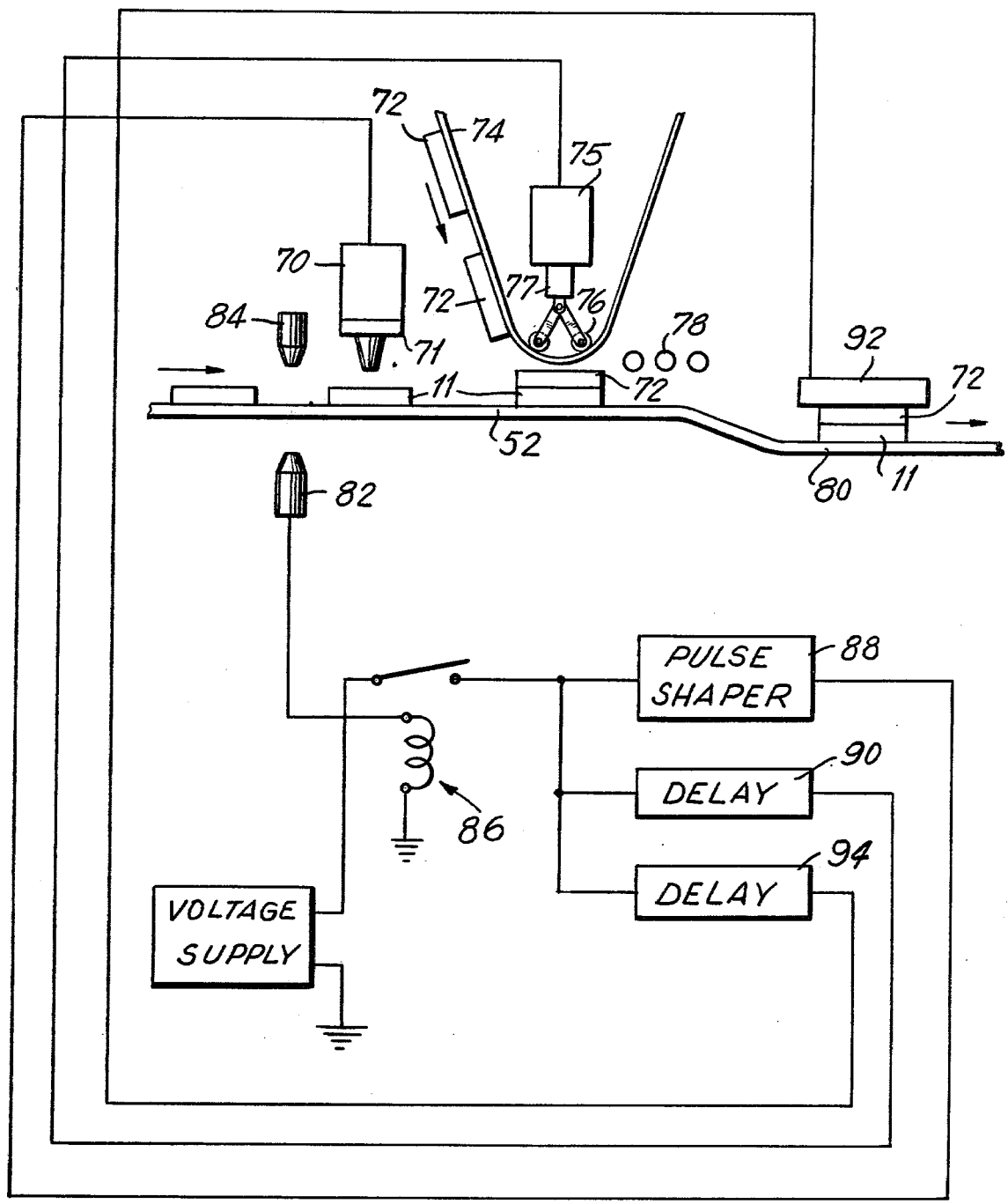
FIG. 6 shows the slide finishing station in greater detail, including glue depositing and cover glass placing means.

Referring now to the drawings, a system for processing and finishing stained glass slides includes a staining rack 10 for receiving stained slides 11 and includes means for discharging the stained slides 11 therefrom, the staining rack 10 being best seen in FIG. 1, conveying means 12, best seen in FIG. 5, for receiving the discharged stained slides 11 from the staining rack 10, and for transporting the stained slides 11 in a direction away from the staining rack 10, and a slide finishing station, best seen in FIGS. 5 and 6 which cooperates with the conveying means 52. The slide finishing station includes means for depositing glue onto the stained slide 11. The stained slide 11 carries the glue and means are provided for applying a cover glass 72 to the glue carrying slide 11.

Figure 2:
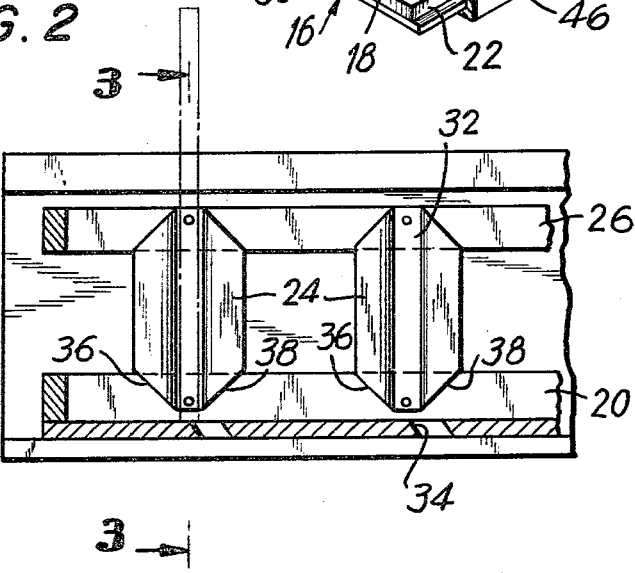
FIG. 2 shows a portion of the staining rack with the slide holders in an upright position.
Figure 3:
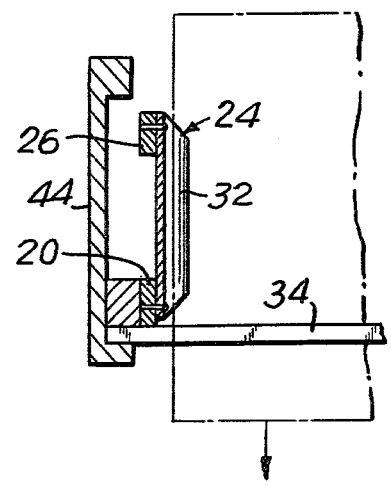
FIG. 3 shows a cross-section of FIG. 2 along the lines 3—3.

The staining rack, which is best seen in FIGS. 1, 2 and 3, includes a longitudinal frame 16 which has a floor 18. The floor 18 has longitudinal edges, a first longitudinal bar 20, a second longitudinal bar 22 attached to the floor 18 in the vicinity of the floor's longitudinal edges, respectively. An equal number of longitudinal slide holder elements 24 are provided on each side of the box; each slide holder element 24 has lower and upper edge portions, respectively. The lower end portions of the slide holder elements 24 are pivotably attached to the inner side of the first bar 20.

A third longitudinal bar 26 and a fourth longitudinal bar 28 are pivotably attached to the upper end portions of the slide holder elements 24. At least one link 30 joins the bars 26 and bars 28. The slide holder elements 24 can thus be moved in unison from a first position inclined at a first angle from the vertical to a second position inclined at a second angle from the vertical, by displacement of the link 30, for example.

Each of the slide holder elements 24 is formed with a rack-inwardly facing longitudinal groove 32, and the floor 18 is formed with a plurality of slits 34. Each of the slits 34 extends from approximately the pivotal attachment of one of the slide holder elements 24 on the first bar 20, to the pivotal attachment of another of the slide holder elements 24 on the second bar 22. A slide 11 may be inserted between two slide holder elements 24 which are disposed opposite one another.

Figure 4:
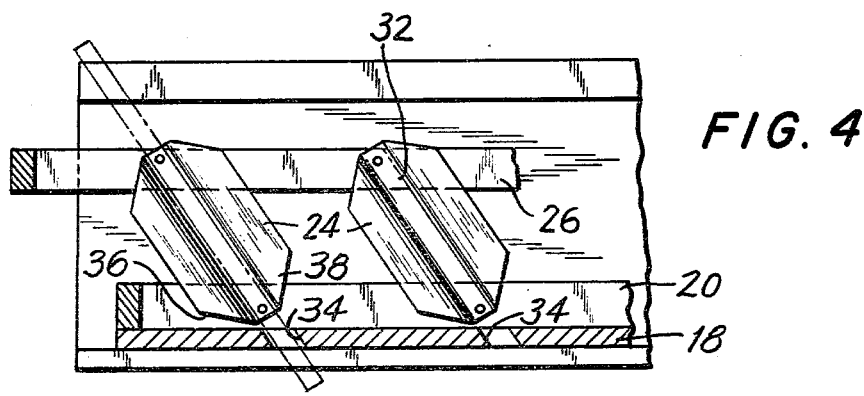
FIG. 4 corresponds to FIG. 3, but with the slide holders in an inclined position.

Each of the slide holder elements 24 is formed with slanted edges 36 and 38; the slanted edge 36 acts as a limit stop and abuts the floor 18 in the first position of the slide holder elements 24, for example, when the slide holders 24 are moved to the left, as shown in FIG. 4.

The slanted edge 38 is substantially symmetrical with the slanted edge 36 about the longitudinal groove 32. For greater rigidity of the structure it is preferable that a link 40 joins the bars 26 and 28.

The staining rack includes a housing 42 which has a first longitudinal portion 44 and a second longitudinal portion 46; a housing end portion 48 joins the longitudinal portions 46 and 44 together and the longitudinal bars 20 and 22 are attached to the longitudinal portions 44 and 46, respectively.

The end portion 40 acts effectively as a limit stop in the second position of the slide holders 24.

Referring now to FIG. 5 which illustrates schematically the conveying means 12 it will be seen that a rack support 48 is provided with an opening 50. The staining rack 10 may be moved across the opening 50 and the slide holder elements 24 are then positioned in either the first or second position, depending on the rearward or forward placement of the staining rack. The rack support opening 50 is sufficiently wide for a slide 11 inserted into the staining rack slide holder elements 24 to drop therethrough.

A first propelling means 52 is disposed below the rack support 48 and a second propelling means 54 has an inclined position and may be placed in the vicinity of the rack support 48 and of the propelling means 52. The dropped slide 11 then lands on the propelling means 54 and is pushed by the latter onto the propelling means 52. Successively dropped slides 11 occupy separate positions on the propelling means 52 and the latter may be moved at a predetermined velocity.

Figure 5A:
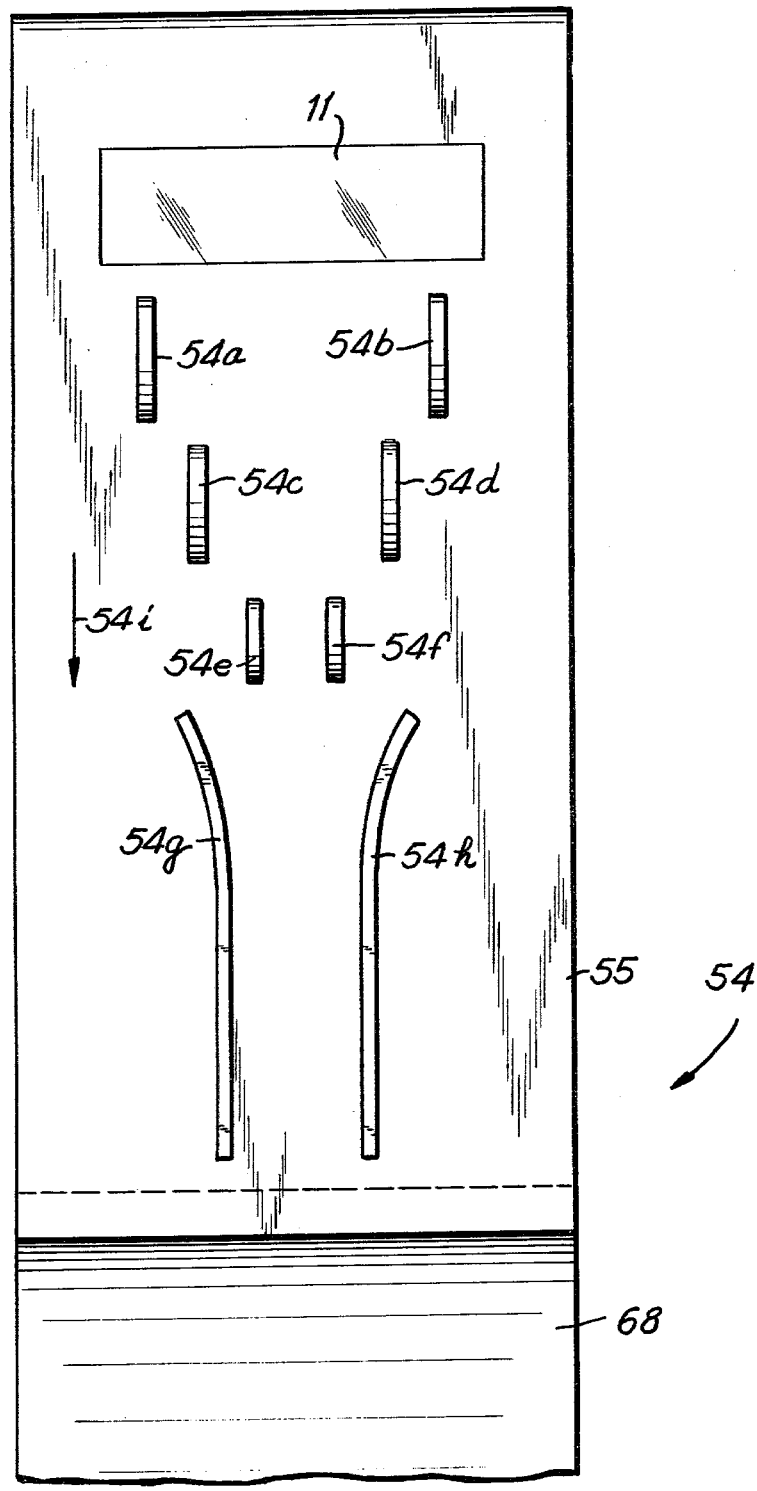
FIG. 5a is a plan view of the inclined belt together with an arrangement for turning the slide.

After the slide 11 has dropped onto the propelling means 54, it becomes rotated through an angle of substantially 90° with the arrangement shown in FIG. 5a. When the slide 11 drops out of the staining rack and reaches the propelling means 54, the longitudinal sides of the slide are substantially normal to the direction of motion of the propelling means 54, shown by the arrow 54i. However, when passing through the finishing station, it is advantageous for the slide 11 to be oriented so that its longitudinal edges are parallel to the direction of motion of the propelling means 52, which is identical to the direction of the arrow 54i. To rotate the slide 11 for this purpose, rotating wheels or rollers 54a and 54b are provided, so that the rotational speed of 54a exceeds that of 54b. In view of the difference in rotational speed of the two rollers 54a and 54b, the slide 11 is turned counterclockwise when viewing the plane of FIG. 5a. After the slide has been advanced in the direction of arrow 54i while being partially turned counterclockwise, the slide reaches rollers 54c and 54d having speeds which differ as the aforementioned rollers 54a and 54b, whereby the rotational speed of 54c is greater than that of 54d. As a result, the slide 11 becomes further turned and reaches rollers 54e and 54f. These latter rollers turn the slide substantially through the last portion of the 90° turn, and feed the slide to guides 54g and 54h. These guides function to align the slide correctly, so that the longitudinal or longer sides of the slide 11 are parallel to the direction of the arrow 54i, when the leading transverse edge of the slide 11 reaches the belt 68 of the propelling means 54. Consequently, the slide 11 is progressively turned through the 90° angle by the rollers 54a–54f. These rollers project substantially through the planar surface on which the slide 11 drops, so as to come into contact with the slide for the purpose of advancing the slide and progressively turning it. The turning unit 55 is mounted adjacent to the continuous belt 68 in the relationship shown in FIG. 5.

The propelling means 52 includes a first roller 56 and a second roller 58 and a continuous belt 60 which links the rollers 56 and 58. A plurality of ridges 62 are disposed on the belt 60 for a slide 11 to be positioned between adjacent ridges 62. The secong propelling means 54 includes a third roller 64 and a fourth roller 66, and a continuous belt 68 which links the rollers 64 and 66.

Referring now to FIGS. 5 and 6, the means for depositing glue onto the stained slide 11 includes a peristaltic dispenser means 70 which is activated upon the slide 11 having reached a predetermined position. The means for applying a cover glass 72 to the stained slide 11 includes a tape 74 which has a property so that glass may adhere thereto. The tape 74 may be moved at the same predetermined velocity as the first propelling means 52, and the cover glass 72 may be attached to the tape 74. The tape 74 with the attached cover glass 72 may be positioned and passed over the propelling means 52 for the cover glass 72 to be aligned and to make contact with one of the dropped slides 11. Roller means 76 may be passed over the cover glass holding tape 74, when the cover-glass holding tape 74 is positioned over one of the drop slides 11 for exerting pressure on the tape 74 so that the cover glass 72 becomes transferred from the tape 74 to the stained slide 11. The glue has an adhesive property which exceeds the adhesive property of the tape 72 and a set of heatable pressure rollers 78 are disposed in the vicinity of the roller means 76. The stained slide 11 with the cover glass 72 attached, may be passed over a support 80 and below the pressure rollers 78 for the slide 11 and the cover glass 72 to be laminated together.

The dispenser 70 is in the form of a glue reservoir or bottle provided with a solenoid valve 71, for example. The solenoid valve is opened for a predetermined interval to allow glue to escape from the reservoir or bottle, and to be applied or spread onto the slide 11 passing beneath the opening of the reservoir or bottle. The solenoid valve is a conventional element which, when actuated by an electrical signal, for example, will provide an opening for glue to pass therethrough.

For purposes of aiding the separation of the cover glass 72 from the carrying tape 74, an electromagnetic actuator 75 is provided. This actuator is of conventional construction and has an armature 77 which functions as a plunger directed against the roller means 76, when an electrical signal is applied to the actuator. Thus, this conventional actuator has a solenoid, which when energized, causes the armature 77 to be displaced and directed against the roller means 76. By striking the roller means 76, in this manner, the cover glass 72 receives a small shock, for example, which serves to aid in the separation of the cover glass from the adhesive holding tape 74. The electromagnetic actuator 75, as well as the solenoid valve 71 are both well known in the art and are commercially available.

For purposes of applying glue to the moving slide 11 during the proper time interval, and to apply the armature or plunger 77 against the roller means 76 at the correct time instant, a photoelectric cell 82 has a light beam directed onto it, so that the light intensity impinging from the source 84 on the cell is interrupted by the passage of a slide 11. The photoelectric cell 82, operating in conjunction with the source 84 may be adjusted so that when a slide 11 passes through the crossing light beam, a pulse is generated by the cell 82 on the basis of a diffused area on the slide, the presence of a specimen on the slide, or the change in light intensity resulting when the edge of the slide is brought into the light beam. The pulse output from the photoelectric cell 82 may be applied to a sensitive relay 86 which when actuated applies a control voltage to the solenoid valve 71, through a pulse shaper 88. The pulse shaper 88 serves to modify the pulse so that it has a time duration corresponding to the desired time interval during which the solenoid valve is to remain open for purposes of spreading an adequate amount of glue onto the bypassing specimen slide 11.

Upon actuation of the relay 86 by a pulse from the photoelectric cell 82, a pulse may also be applied to the actuator 75 through a delay element 90. A laminating unit 92 may, similarly receive a pulse through a further delay circuit 94, for the purpose of carrying out a laminating procedure at the proper time instant. The delay provided by the element 90 may be selected or adjusted on the basis of the time interval found to prevail between the instant that a slide 11 is beneath the glue dispensing means 70 and the instant that the cover glass 72 is to be separated from the tape 74 and applied over the slide 11. The delay of element 94 may be similarly set or adjusted so as to correspond to the time interval elapsing in the movement of the slide from the position beneath the glue dispensing means 70 and the laminating support 80. The delay elements 90 and 94 may be in the form of conventional delay lines that are well known in the art. Pulse shapers such as the element 88 for adjusting the duration of a pulse to a predetermined duration, are also conventional devices well known in the art.

The finished glass slides 11 equipped with cover glasses 72 then proceed to the point on continuous belt 60 where they drop off to be collected (not shown) for study and/or storage.

While there has been shown what is considered to be the preferred embodiment of the invention, it will be obvious that modifications may be made which come within the scope of the disclosure of the specification and the appended claims.

What is claimed is:

1. A process for finishing stained glass slides comprising the steps of: inserting stained slides into pivotable slide holders elements in a rack, moving said rack over an opening in a rack support and discharging a respective inserted stained slide from said rack through an opening in the bottom of said rack by pivoting said slide holder elements, said slide holder elements for said respective inserted slide overlying said rack support opening, said respective slide dropping onto a conveying means; repeating said steps of moving said rack and discharging a respective slide; transporting said slides on said conveying means in a direction away from said rack; depositing glue onto said slides while on said conveying means after being transported away from said rack; and applying a cover glass to each of said slides while on said conveying means so that each cover glass adheres to each slide by means of said glue.

2. A process as defined in claim 1 including the step of carrying said cover glass on a tape; and separating said cover glass from said tape when said slide is beneath said cover glass.

3. A process as defined in claim 2 including the step of applying a mechanical impulse to said tape for separating said cover glass from said tape.

4. A process as defined in claim 3 including the step of applying said impulse at a predetermined time interval after applying glue to said slide.

5. A process as defined in claim 4 including the step of laminating said slide and said cover glass together at a predetermined time after covering said slide with said cover glass.

6. A process as defined in claim 1 including the step of applying pressure to said cover glass after being applied to said slide.

7. A system for processing and finishing stained glass slides comprising:
    (a) a staining rack for receiving stained slides and including slide holder elements movable in unison from a first position inclined at a first angle from the vertical to a second position inclined at a second angle from the vertical and means for discharging the stained slides therefrom;
    (b) conveying means for receiving the discharged stained slides from said staining rack, and for transporting the stained slides in a direction away from said staining rack said conveying means comprising:
        a rack support formed with an opening, said staining rack being movable across said opening, said slide holder elements being in one of said first and second positions, the rack opening being sufficiently wide for a slide inserted into the staining rack slide holder elements to drop therethrough; a first propelling means disposed below said rack; and
        a second propelling means having an inclined position and being placeable in the vicinity of said rack and of said first propelling means, whereby the dropped slide lands on said second propelling means, and is pushed by the latter onto said first propelling means being movable at a predetermined velocity and
    (c) a slide finishing station cooperating with said conveying means, said slide finishing station including means for depositing glue onto the stained slide, the stained slide carrying the glue, and means for applying a cover glass to the glue-carrying slide.

8. A system according to claim 1 wherein said first propelling means comprises first and second rollers, a continuous first belt linking said rollers, and a plurality of ridges disposed on said belt for a slide to be positionable between adjacent ridges, and wherein said second propelling means comprises third and fourth rollers, and a continuous second belt linking said third and fourth rollers.

9. A system according to claim 1 wherein the means for depositing glue onto the stained slide includes peristaltic dispenser means activatable upon the slide having reached a predetermined position, and wherein the means for applying a cover glass to the stained slide includes a tape having a glass-adhesive property, and being movable at said predetermined velocity, the cover glass being attachable to said tape, said tape with the attached cover glass being positionable and passable over said first propelling means, for the cover glass to be alignable, and to make contact with one of the dropped slides, and roller means passable over the cover-glass holding tape, said cover-glass holding tape being positionable over said one of the dropped slides for exerting pressure on said tape for the cover glass to be transferred from said tape to the stained slide, the glue having an adhesive property exceeding the adhesive property of said tape, and further comprising a set of heatable pressure rollers disposed in the vicinity of said roller means, the stained slide having the cover glass attached thereto being passable over a support and below said pressure rollers for the slide and the cover glass to be laminated together.

* * * * *